(12) United States Patent
Campo et al.

(10) Patent No.: US 6,451,612 B1
(45) Date of Patent: Sep. 17, 2002

(54) METHOD FOR DETERMINING A LEVEL OF TREATMENT WITH OZONE OF A LIQUID TO BE TREATED

(75) Inventors: Philippe Campo, Montigny le Bretonneux; Aurélie Grimberg, Saint-Cloud; Jean-Marc Rabillier; Maurice Rignon, both of Guyancourt, all of (FR)

(73) Assignee: L'Air Liquide Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 09/604,830

(22) Filed: Jun. 28, 2000

(30) Foreign Application Priority Data

Nov. 22, 1999 (FR) .............................. 99 14619

(51) Int. Cl.[7] .............................................. G01N 31/22
(52) U.S. Cl. ....................... 436/135; 210/739; 210/760; 210/96.1; 422/3; 436/174
(58) Field of Search .................................. 210/696, 739, 210/760, 764, 96.1, 192; 422/3, 119; 436/135, 174

(56) References Cited

U.S. PATENT DOCUMENTS

| | | | | |
|---|---|---|---|---|
| 4,409,183 A | | 10/1983 | Fischer | ..................... 422/68 |
| 4,849,178 A | * | 7/1989 | Azuma | ..................... 422/69 |
| 5,324,666 A | | 6/1994 | Siepmann et al. | ............. 436/62 |
| 5,403,602 A | | 4/1995 | Endico | ..................... 426/231 |
| 5,415,783 A | * | 5/1995 | Johnson et al. | ............. 210/699 |
| 6,235,206 B1 | * | 5/2001 | Chan et al. | ................. 210/739 |
| 6,235,207 B1 | * | 5/2001 | Conrad | ..................... 210/742 |
| 6,277,291 B1 | * | 8/2001 | Burris | ..................... 210/760 |

* cited by examiner

Primary Examiner—Peter A. Hruskoci
(74) Attorney, Agent, or Firm—Burns, Doane, Swecker & Mathis, L.L.P.

(57) ABSTRACT

Method for the determination of a level of treatment with ozone of a liquid to be treated, comprising the steps of:

a) storing the liquid to be treated, the liquid having at least one of an initial dissolved oxidant and ozone content of $C_i$;

b) manufacturing an ozonized water mother solution with a given and constant content of dissolved ozone $C_m$;

c) withdrawing a volume $V_m$ of the mother solution and admixing it with a sample of the stored liquid with a volume of $V_i$;

d) measuring at least one of the content $C_f$ of dissolved residual oxidants and dissolved ozone in the sample after admixture with the volume $V_m$ of the mother solution, immediately after at least one of addition and at predetermined, regular or irregular time intervals after the addition;

e) determining the level of treatment to be applied to the liquid as a function of the value of the quantity $C_f - C_i$.

5 Claims, 2 Drawing Sheets

METHOD FOR DETERMINING A LEVEL OF TREATMENT WITH OZONE OF A LIQUID TO BE TREATED

CROSS REFERENCE TO RELATED APPLICATION

The present application claims the benefit of French patent application 99 14619 filed Nov. 22, 1999, the disclosure of which is hereby incorporated by reference.

BACKGROUND OF THE INVENTION

(I) Field of the Invention

The present invention relates to the field of the treatment with ozone of liquids, which treatment with ozone perhaps, as is known, is used in a very large number of industrial applications: for example in connection with the environment (water and effluent treatment, and the like), in the treatment of foodstuffs with ozone (liquid foods, in particular drinks, washing foodstuffs with ozonized water, such as seafood or also fruit and vegetables) or in aquaculture and pisciculture (rearing sites or all or part of the water which feeds the rearing pond or ponds of the user site is treated with ozone).

(II) Description of the Related Art

The treatment of piscicultural or aquacultural rearing sites with ozone has formed the subject of very extensive literature. Reference can be made, for example, to French Patent Application on behalf of Applicant Company FR-99 06567, which is concerned with the ozonization of rearing sites operating in closed circuits. The literature emphasizes the considerable advantage in treating water which feeds the ponds (health advantages, productivity, and the like). It is nevertheless a fact that difficulties and questions remain relating to the use of ozonization, treatments. These difficulties and questions are related in particular to the fact that the residual oxidizing components of a treatment with ozone may be toxic to the farmed species, whether it is the residual ozone itself in the medium or all the oxidizing by-products originating from the ozonization reactions of ozone with the medium (in particular salts, in the case of seawater).

It is also necessary to take into consideration the fact that, when ozone is injected into water (or any other liquid), part of this ozone is immediately consumed by the water in attacking organic matter, such as colors or bacteria, or in reactions with salts present in the water. Only subsequent to such consumption does the injection of ozone actually give rise to an ozone or oxidant residue which can be taken into account in carrying out the treatment targeted by the application under consideration.

The targeted treatment can, of course, be highly variable, depending on the application under consideration and depending on the specifications pursued by each user site. The treatment carries out one or more actions from the following actions: bleaching, disinfection, deodorization or water purification of the water (removal of toxic or undesirable components).

A person skilled in the art commonly speaks, with regard to this immediate consumption of ozone by the water (or by the liquid in the case of the most general application), of "ozone demand" of the water under consideration.

In what follows, reference is made to the case of the treatment of a water while keeping in mind the fact that these treatments (and the notion of "ozone demand" which is associated) applies more generally to liquids of highly varied origins.

It may therefore be said, with regard to this "ozone demand" of the water to be treated:

that this demand represents the amount of ozone immediately consumed (it may even be said "swallowed") by the water;

in other words, this "ozone demand" is the amount of ozone which can be introduced into the water before the appearance of a residue (of ozone and/or of oxidant) in the water;

it depends on the quality of the water to be treated;

the determination of this ozone demand of the water to be treated and of the persistence of the resulting oxidant or ozone residue makes it possible to calculate the ozone treatment dose to be applied to the water under consideration.

The level of treatment to be applied to the water under consideration will therefore be determined as a function:

of the oxidant or dissolved ozone residue to be maintained in the water after having satisfied the instantaneous demand of the water under consideration, in other words of the effectiveness desired according to the treatment under consideration (for example, amount starting from which the desired disinfecting effect is effectively obtained);

of the safety of the site of use under consideration (local legislation or alternatively, for example, in the context of fish farms not tolerating any oxidants and/or ozone residue beyond a given residence time $\Delta T$).

The literature records a number of existing solutions for the determination of the ozone demand of a water to be treated, which solutions will be described in more detail in the context of FIGS. 1 and 2 hereinbelow, FIG. 1 being devoted to a determination solution which may be described as a "batch"-style solution, whereas FIG. 2 is devoted to a determination solution which may be described as a "continuous" determination.

According to the first prior method for determination of the ozone demand of a water to be treated, a gas with a predetermined ozone content is injected into a sample of the water to be treated, the water sample is stirred and then, on the one hand, the dissolved ozone content of the water is determined and, on the other hand, the ozone content of the gas phase lying above the liquid water phase in the sample is determined.

The ozone demand is then determined by a conventional conservation equation relating to the initial amount of ozone injected through the gas, the dissolved ozone content of the water after stirring and the gaseous ozone content of the as phase existing above the liquid phase of the sample.

The disadvantages of such a "batch"-style determination method are related in particular to the accuracy necessary in knowing the ozone content of the ozonized gas introduced but also to the fact that, in order to quantitatively determine the sample (in its liquid phase and in its gas phase), it is necessary to withdraw liquid and gas, which already per se (in the fact of withdrawing alone) falsifies the result of the measurement since ozone then naturally escapes from the liquid medium.

According now to the second so-called "continuous" determination method, the water to be treated, on the one hand, and an ozonized gas, on the other hand, are delivered to a contactor of continuous bubble column type in order to carry out dissolution in the contactor, so as to analyze, at the outlet of the contactor, the water and its dissolved ozone residue, and the non-transferred ozonized gas (outlet gas).

It is then seen that this continuous determination method is certainly reliable and furthermore widely used in the literature but unquestionably exhibits the disadvantage of requiring a large volume of water to achieve equilibrium and also the use of a great deal of equipment (numerous analyzers), therefore being relatively complex and not very compact.

SUMMARY AND OBJECTS OF THE INVENTION:

A particular object of the present invention is to solve the abovementioned technical problems in connection with the determination methods according to the prior art.

The method according to the invention for the determination of a level of treatment (T) with ozone of a liquid to be treated then comprises the implementation of the following measures:

a) there is available a store of the liquid to be treated, the initial dissolved oxidants and/or ozone content of which is $C_i$, b) an ozonized water mother solution with a given and constant volume of dissolved ozone $C_m$ is manufactured (starting from distilled or demineralized water);

c) a volume $V_m$ of the mother solution is withdrawn in order to introduce it into a sample of the store with a volume of $V_i$;

d) the content $C_f$ of residual oxidant and/or dissolved ozone in the sample after the addition of $V_m$ is measured, immediately after addition and/or at predetermined (regular or irregular) time intervals after the addition;

e) the level of treatment to be applied to the liquid is determined as function of the value of the quantity $C_i-C_f$ (thus, as will have been understood, as a function of the difference between the amount of residual oxidants and ozone present in the sample after addition and that initially present in the sample before addition).

As will be clearly apparent to a person skilled in the art, the ozonized water mother solution, in order to be "with a given and constant content of dissolved ozone," will advantageously be obtained at saturation (this being in order to avoid as far as possible self-decomposition phenomena): the saturation of a liquid with a dissolved gas, in this instance ozone, being, as is known, according to Henry's law, a function of the nature of the liquid and of the temperature but also of the partial ozone pressure in the injected gas.

According to one of the embodiments of the invention, the liquid to be treated is a fresh water and the level of treatment T is determined in the following way:

the ozone consumption of the water is evaluated by the expression:

Consumption=$C_m V_m + C_i V_i - C_f (V_m + V_i)$ in mg;

the ozone demand of the water to be treated is deduced therefrom by the following expression: ozone demand= consumption/$V_i$ in mg/l;

a level of treatment T greater than the value of the ozone demand is chosen.

As will be clearly apparent to a person skilled in the art on reading all the above, the level of treatment T greater than the value of the ozone demand will be chosen as a function of each final application and therefore, according to the situation, as a function of the residue desired by the user site and as a function of the persistence of ozone and/or of oxidant in the water to be treated for various residence times (see stage d) above).

According to one of the embodiments of the method in the case of such a fresh water, the level of treatment T greater than the value of the ozone demand is chosen in the following way:

i) the value of the residual oxidants and/or dissolved ozone residue desired by the application under consideration for the water to be treated for its final use is known;

ii) the minimum journey time $\Delta T_{min}$ between the treatment point and the final user point is evaluated for the application under consideration of the water to be treated;

iii) the persistence of the ozone in the water to be treated is evaluated by measuring, in accordance with stage d) at time intervals after the addition, the content $C_f$ of residual oxidants and/or dissolved ozone in the samples after the addition of $V_m$;

iv) a level of treatment T is chosen as a function: of the residual oxidants and/or dissolved ozone residue desired by the application under consideration and of the persistence $C_f$ measured during the preceding stage iii) after an interval $\Delta T_{min}$ after the addition of $V_m$.

According to another of the embodiments of the invention, the liquid to be treated is a seawater and successive iterations are then carried out in order to determine the maximum withdrawal volume $V_m^{max}$ which makes it possible to obtain, immediately after addition, a value of the content $C_f$ substantially identical to that of the content $C_i$, this being done in the following way:

if $C_f$ is greater than $C_i$, the stages c) and d) listed above are repeated with a withdrawn portion with a volume of $V_n$, $V_n$ being less than $V_m$, until a value of the content $C_f$ is obtained which is substantially identical to that of the content $C_i$ (to within approximately 0.01 mg/l or so);

if $C_f$ is substantially identical to $C_i$, the stages c) and d) are repeated with a withdrawn portion with a volume of $V_n$, $V_n$ being greater than $V_m$, as long as the value of the content $C_f$ is substantially identical to the content $C_i$ (to within approximately 0.01 mg/l or so);

the ozone demand of the water to be treated then corresponds to $C_m V_m^{max}/V_i$ (in mg/l);

a level of treatment T equal to the ozone demand is chosen.

According to another of the embodiments of the invention, the water to be treated is a seawater and successive iterations are then carried out in order to determine the maximum withdrawal volume $V_m^{max}$ which makes it possible to obtain, after a predetermined time $\Delta T$ after the addition, a value of the content $C_f$ substantially identical to that of the content $C_i$, this being done in the following way:

if $C_f$ is greater than $C_i$, the stages c) and d) listed above are repeated with a withdrawn portion with a volume of $V_n$, $V_n$ being less than $V_m$, until, after the predetermined time $\Delta T$, a value of the content $C_f$ is obtained which is substantially identical to that of the content $C_i$ (to within approximately 0.01 mg/l or so);

if $C_f$ is substantially identical to $C_i$, the stages c) and d) are repeated with a withdrawn portion with a volume of $V_n$, $V_n$ being greater than $V_m$, as long as the value of the content $C_f$ is, after the predetermined time $\Delta T$, substantially identical to the content $C_i$ (to within approximately 0.01 mg/l or so);

the ozone demand of the water to be treated then corresponds to $C_m V_m^{max}/V_i$ (in mg/l);

a level of treatment T equal to the ozone demand is chosen, and the presence is provided for of a reactor, for holding the water thus treated using the level of treatment T, capable of holding the water thus treated for a time of at least $\Delta T$, before any subsequent use of the water thus treated.

The present invention also relates to a process for the treatment of a liquid by injection into the liquid to be treated of an ozonized gas employing a level of treatment with ozone T, which is characterized in that the level of treatment T to be applied to the liquid is determined by applying the determination method described above.

According to one of the aspects of the invention, the treatment process is targeted at carrying out one or more of the actions from the following actions; a bleaching, a disinfection or a deodorization of the water, and the liquid thus treated is subsequently used for washing foodstuffs or in aquacultural or pisicicultural rearing sites, rearing sites of the type or all or part of the water which feed the rearing pond or ponds of the user site is treated with ozone.

Other characteristics and advantages of the invention will emerge from the following description, given solely by way of illustration and without implied limitation and made with reference to the appended drawings.

Figure 1:
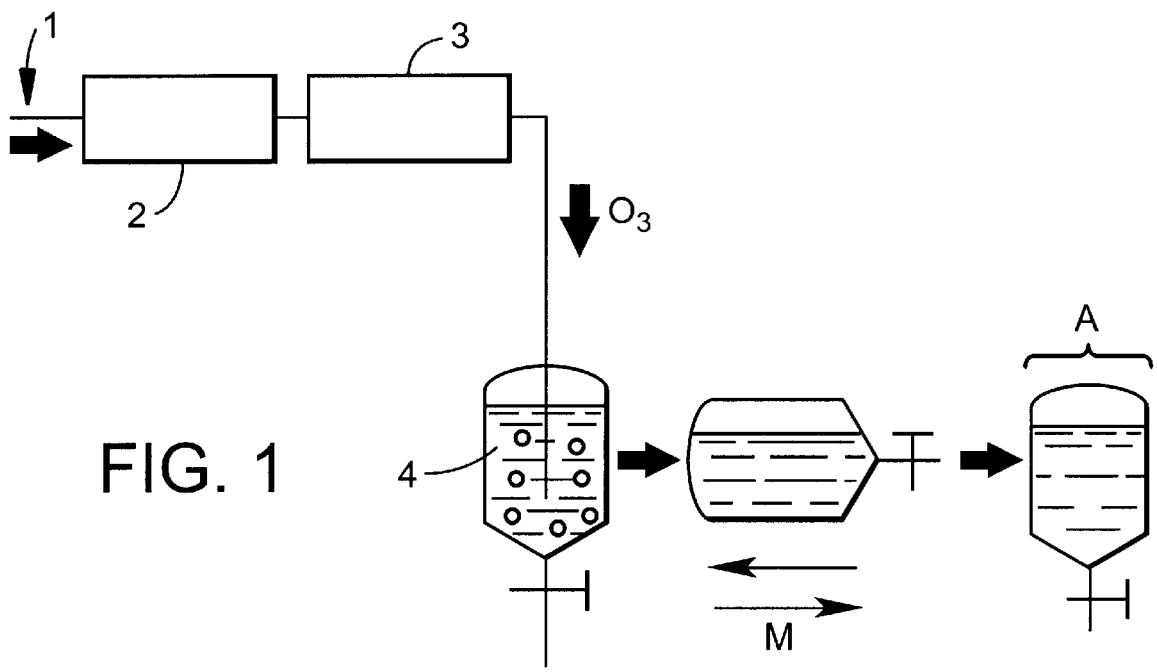
FIG. 1 is a diagrammatic illustration of a method for the determination of the ozone demand according to the prior art, described as the "batch" method.

DETAILED DESCRIPTION OF PREFERRED EMBODIMENTS:

FIG. 1 shows the presence of an inlet 1 for oxygenated gas on an ozonizer 2 capable of producing, at its outlet, an ozonized gas (analyzed by the analyzer 3), which gas is directed to a sample of water 4 (with a volume of $V_i$) in order to be injected therein.

The sample is subsequently subjected to a stirring (mixing) stage in the phase symbolized in the figure by the letter M, in order subsequently to form the subject of an analysis A:

the content of ozone in the ozonized gas emerging from the ozonizer (=$C_g(O_3)$) is determined according to this method, from which the amount of ozone conveyed during an injection time t(=$Q_g(O_3)$) is deduced;

the content of ozone dissolved in the water after stirring (=$C_{water}(O_3)$) is determined, from which the amount of ozone dissolved in the sample $V_i$ under consideration ($V_i \times C_{water}(O_3)$);

the content of ozone in the gas phase present above the water of the sample (=$C_{gas\,ph.}(O_3)$) is determined, from which the amount of ozone present in this gas phase (=$Q_{gas\,ph.}(O_3)$);

finally, the ozone CONSUMPTION of this sample is determined by the conservation equation: $Q_g(O_3)$= $V_i C_{water}(O_3) + Q_{gas\,ph.}(O_3) +$ CONSUMPTION in mg;

the "ozone demand" of the water tested, in mg/l, is then expressed by the expression: ozone demand= CONSUMPTION/$V_i$.

The following comments on this method may then be made:

it requires great accuracy with regard to the amount of ozonized gas introduced;

the conservation equation is based on a withdrawn portion of the gas phase and a withdrawn portion of the liquid phase of the sample, which creates per se an effect described by a person skilled in the art as "stripping" (dissolved ozone escapes from the liquid into the gas phase), thus falsifying in proportion the results obtained.

Figure 2:
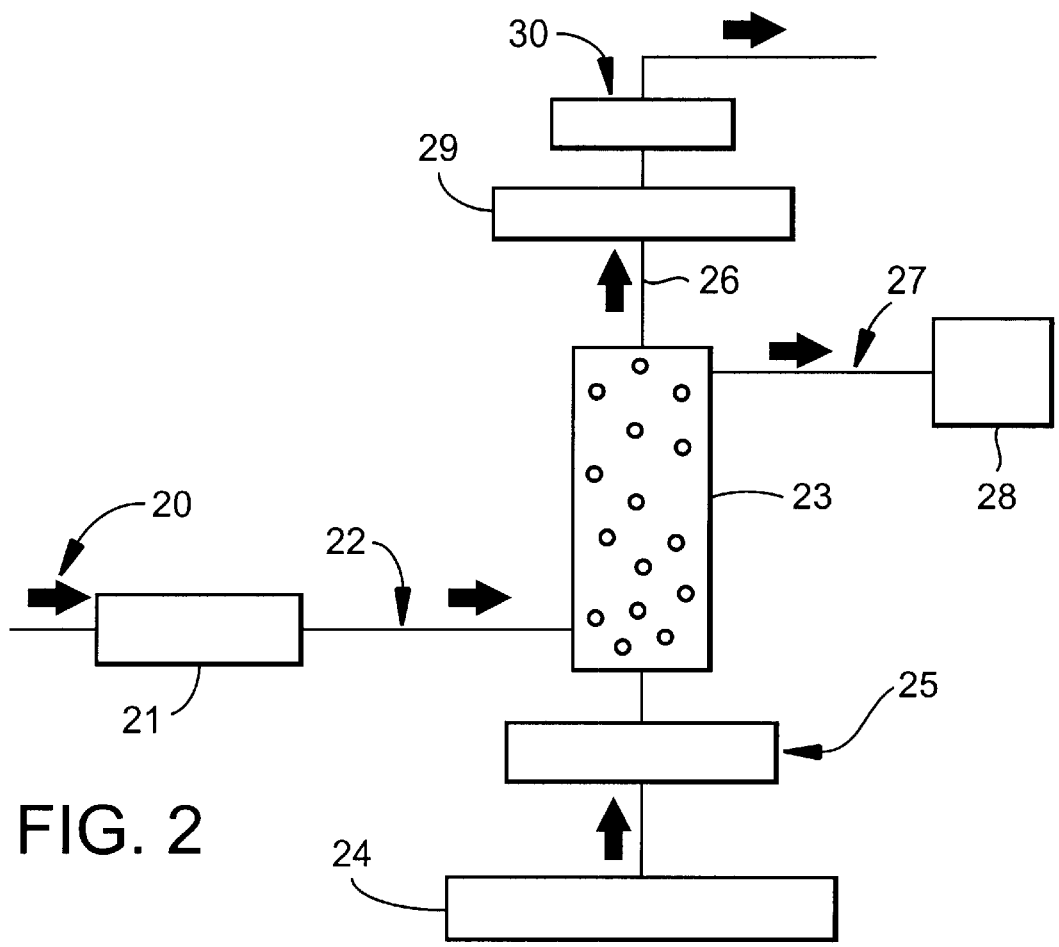
FIG. 2 is a diagrammatic illustration of a method for the determination of the ozone demand according to the prior art, described as the "continuous" method.

FIG. 2 shows the presence of an inlet for water 20 (the ozone demand of which has to be determined) which passes through an analyzer for dissolved ozone 21 before reaching a contactor 23 (for example of the bubble column type), where it encounters an ozonized gas originating from the ozonizer 24/gas analyzer 25 assembly.

The water 27 at the contactor outlet is conveyed to an analyzer for dissolved ozone 28, whereas the undissolved gas 26 which exits from the contactor is directed to an assembly composed of an analyzer 29 and a detoxification system 30, before being discharged to the outside.

The process for the determination of the "ozone demand" according to this method then employs the following stages:

the amount of ozone dissolved in the starting water and therefore the amount of dissolved ozone entering per unit of time ($Q_{water}(O_3)i$ in mg/min) are determined according to this method (by virtue of the analyzer 21);

the amount of ozone in the gas originating from the ozonizer 24 and therefore the amount of gaseous ozone entering per unit of time ($Q_{gas}(O_3)_i$ in mg/min) are determined by virtue of the analyzer 25;

the amount of dissolved ozone in the outlet water of the contactor and therefore the amount of dissolved ozone per unit of time ($Q_{water}(O_3)_f$ in mg/min) are determined by virtue of the analyzer 28;

the amount of ozone in the outlet gas of the contactor and therefore the amount of gaseous ozone per unit of time ($Q_{gas}(Q_3)_f$ in mg/min) are determined by virtue of the analyzer 29;

the ozone consumption of this water is then determined continuously by the conservation equation:

CONSUMPTION=$Q_{water}(O_3)_i + Q_{gas}(O_3)_i$-$Q_{water}(O_3)_f$-$Q_{gas}(O_3)_f$ in mg/min;

the "ozone demand" of the water tested, in mg/ml, is then expressed by the expression: demand= CONSUMPTION (mg/min)/flow rate of water (l/min).

The following comments on this method may then be made:
- the technical difficulties related to the continuous nature of the installation have already been noted A(volume of water, time to reach equilibrium of the system, distribution of the residence times in the bubble column, and the like);
- the analytical equipment required (4) is very bulky and expensive;
- the method in its entirety is for this reason complex and not very compact.

The method for the determination of the "ozone demand" of a water to be treated according to the present invention will be illustrated, in what follows, by virtue of FIG. 3. In all which follows, the quantitative determinations of ozone and/or of oxidants dissolved in the water are carried out by use of a Hach determination of the total chlorine by the colored reagent DPD (measurement carried out at 530 nm).

Figure 3A:
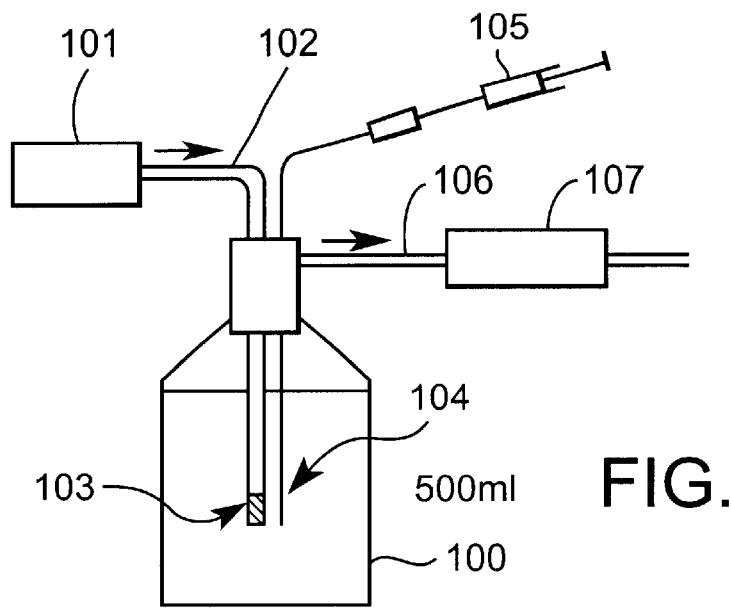
FIG. 3 is a diagrammatic illustration of an embodiment of the method for the determination of the ozone demand according to the invention.

The manufacture of the mother solution, obtained here starting from 500 ml of demineralized water, has been illustrated in FIG. 3A.

A bottle 100 (comprising the starting 500 ml of demineralized water) has present: an inlet line 102 for ozonized gas originating from an ozonizer 101, the line 102 being equipped at its end with a porous diffuser 103; a capillary line 104, allowing the withdrawal of a volume $V_m$ of mother solution through a syringe 105 (method of withdrawal chosen in order to avoid bringing into contact with the surrounding air and thus to retain a constant concentration $C_m$ in the mother solution; a line 106 for discharge of the undissolved gas phase which passes through a detoxification system 107.

As already indicated above in the context of the present description, the mother solution is advantageously saturated at the pressure and temperature conditions used; the ozonized gas then arrives continuously throughout the duration of the operations.

Figure 3B:
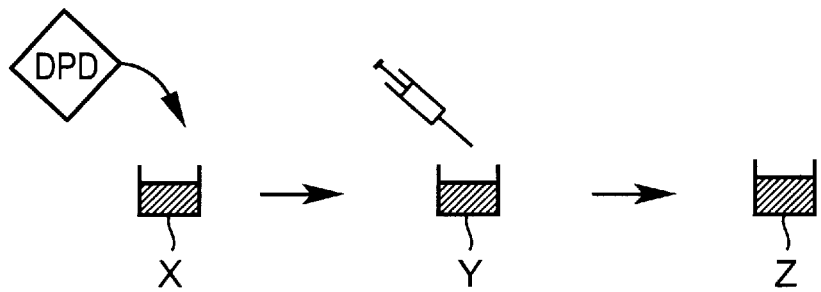

Various operations undergone by a sample of water to be treated are considered in FIG. 3B:
- stage X: control sample of water to be treated (in this instance 25 ml), the initial content of dissolved residual oxidants and/or ozone of which is quantitatively determined (colored reagent DPD);
- stage Y: sample of water to be treated (9n this instance 23 ml), to which a withdrawn portion $V_m$ (in this instance 2 ml) of mother solution is added via a syringe (FIG. A);
- stage Z: the sample originating from stage Y (after addition) is quantitatively determined for dissolved residual oxidants and/or ozone (colored reagent DPD). The quantitative determination takes place immediately after addition of the mother solution or else after a predetermined time interval. It is thus possible, in order to monitor the content of the residual oxidants and/or ozone residue over time, to manufacture several samples in stage Y in order to subsequently quantitatively determine them in Z at time intervals, I.e. residence times (ex: immediately after addition, at 1, 2, 3, 5 and 10 min, and the like).

Figure 3C:
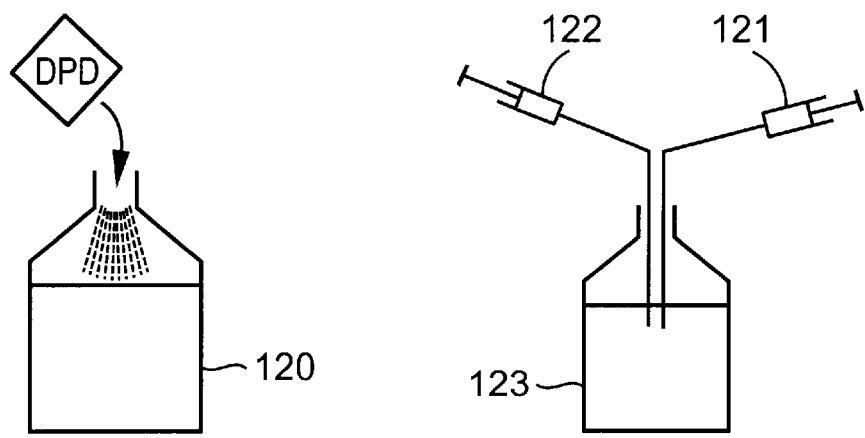

FIG. 3C for its part gives a precise description allowing better visualization of the stages of FIG. 3B:
- for stage X: the bottle 120 of control sample of water to be treated, the initial content of dissolved residual oxidants and/or ozone of which is quantitatively determined with addition of the colored reagent DPD; for stage Y: the bottle 123 comprising a sample of water to be treated (23 ml), to which a withdrawn portion $V_m$–2 ml of mother solution is added via the syringe 121 and the dissolved residual oxidants and/or ozone residue of which is/are subsequently quantitatively determined, at the desired time (stage Z) by virtue of the addition of the colored reagent DPD (syringe 122).

As will have been understood in light of the above, the method for the determination of the "ozone demand" of a liquid to be treated according to the present invention introduces significant advantages with respect to the prior methods recalled above:
- the method does not require knowledge of the initial characteristics of the ozonized gas used, only the known and stable characteristics of the mother solution mattering;
- the addition of mother solution, the addition of reagent DPD and the spectrophotometric analysis are carried out in a single sample cell (that of the spectrophotometric equipment used), without requiring decanting or withdrawal of liquid and gas phases, therefore avoiding the errors and artefacts related to the handling operations indicated above in the case of the prior art;
- it is precisely the credit of the present invention to have thought out and shown that it is advantageous to involve the addition of calibrated and controlled liquid phase in order to determine the "ozone demand" of the liquid to be treated and, starting from there, the level of treatment to be applied.

A first example of the implementation of the method for the determination of the ozone demand according to the invention was carried out on fresh river water (for a piscicultural application operating in an open circuit) under the following experimental conditions:

a) manufacture of the mother solution starting from distilled water: a saturated solution is manufactured with $C_m$=8.9 mg $O_3$/l;

b) initial content ($C_i$) of oxidants in a 25 ml sample of the fresh water to be treated: 0.007 mg/l sample of the fresh water to be treated: 0.007 mg/l (spectrophotometric measurement: 0.01 mg $Cl_2$/l);

c) $V_m$=2 ml of ozonized water mother solution (2 ml of mother solution therefore comprises 0.018 mg of ozone) are added to a sample $V_i$ of 23 ml of water to be treated;

d) after addition of the reagent DPD, the content of oxidants in the total volume of 25 ml is measured: $C_f$=0.71 mg $O_3$/l, therefor giving 0.018 mg of ozone present in this 25 ml sample (spectrophotometric measurement: 1.05 mg $Cl_2$/l);

e) it is deduced therefrom that the ozone has not been consumed, this being because all the ozone which had been added through the 2 ml of mother solution is re-encountered, and it is concluded therefrom that the "instantaneous ozone demand" of this fresh water is negligible. This result is in good agreement with the fact that the water to be treated was of good quality, naturally with a not very high load.

f) for the piscicultural installation under consideration which uses this fresh water, the minimum residence time $\Delta T_{min}$ (journey time) between the treatment point and the point of use was 20 min and a zero ozone residue was desired fro the fish after this time $\Delta T_{min}$;

g) the persistence of the ozone in the water to be treated was then estimated by carrying out measurements on 3 samples by addition of reagent DPD at t=5 min, t=10 min and t=20 min after the addition of $V_m$ (each sample, of course, being stored stoppered and sheltered from the light during each residence time tested).

The following results are then obtained:

| t (min) | Residual O$_3$ (mg/l) | Consumption (%) |
|---|---|---|
| 0 | 0.71 | /// |
| 5 | 0.21 | 70 |
| 10 | 0.05 | 93 |
| 20 | 0.01 | 100 | h) the level of treatment T is then determined as a function, on the one hand, of the targeted disinfecting objective and, on the other hand, of the safety conditions for the fish, providing a zero$_{ozone}$ residue after 20 minutes: a level of treatment of 0.7 mg O$_3$/l is therefore highly suitable for such a specification.

A second example of the implementation of the method for the determination of the ozone demand according to the invention was carried out on seawater from a fish farm operating in a closed circuit, the example having been carried under the following experimental conditions:

a) manufacture of the mother solution starting from distilled water: a saturated solution is manufactured with $C_m$=5.4 mg O$_3$/l (spectrophotometric measurement: 0.64 mg Cl$_2$/l);

b) initial content of oxidants in a 25 ml control sample of the seawater to be treated $C_i$=0.045 mg/l;

c) the results obtained (measurement of the total oxidants residue 1 min after the addition of a withdrawn portion $V_m$ of mother solution) are collated in the table below, where the symbols used have the following meanings:

$V_m$: ml of mother solution which are added to a sample $V_i$ of seawater to be treated (such that $V_i+V_m$=25 ml);

T: level of treatment =mg of ozone which are added (via the withdrawn portion) per liter of seawater to be treated ($V_i$)l C: result of the measurement of total oxidants residue (in mg/l) in the 25 ml bottle.

| $V_m$ (ml) | T (mg/l) | C (mg/l) |
|---|---|---|
| 5.6 | 1.20 | 0.12 |
| 4.2 | 0.90 | 0.11 |
| 3.2 | 0.70 | 0.08 |
| 2.5 | 0.55 | 0.08 |
| 1.5 | 0.33 | 0.06 |
| 1.2 | 0.26 | 0.05 |

The fact is deduced from this table that a level of treatment for this seawater circulating in a closed circuit of 0.33 mg O$_3$/l would be suitable for this piscicultural application by ensuring an absence of oxidizing residue ($C_f$ substantially identical to $C_1$, to within approximately 0.01 milligram/l or so).

If it were decided to adopt a level of treatment of greater than 0.33 mg O$_3$/l of water (for example 0.55 or 0.70), a measurement of the persistence of the oxidants would have to form the basis and it would be necessary to provide for the presence of a tank for holding the treated water for a few minutes, allowing the disappearance of the residue before any subsequent contact of the water, thus treated, with the fish.

It should be noted that it could also be possible, while adopting a level of treatment greater than 0.33 mg O$_3$/l of water, not to choose the solution of a holding tank but to adopt, on the other hand, a method of exhausting the oxidants and ozone residue from the water after treatment, this being carried out by the addition of a reagent, such as a compound from the bisulphites family, or by passing through an active charcoal filter.

What is claimed is:

1. Method for the determination of a level of treatment with ozone of a liquid to be treated, comprising the steps of:

a) storing said liquid to be treated, said liquid having at least one of an initial dissolved oxidant and ozone content of $C_i$;

b) manufacturing an ozonized water mother solution with a given and constant content of dissolved ozone $C_m$;

c) withdrawing a volume $V_m$ of the mother solution and admixing it with a sample of said stored liquid with a volume of $V_i$;

d) measuring a content $C_f$ of at least one of dissolved residual oxidants and dissolved ozone in said sample after admixture with the volume $V_m$ of the mother solution, immediately after at least one of addition and at predetermined, regular or irregular time intervals after the addition; and e) determining the level of treatment to be applied to the said liquid as a function of the value of the quantity $C_f$-$C_i$.

2. The method according to claim 1, comprising determining the level of treatment of fresh water, comprising the steps of:

evaluating consumption of the ozone by said water to be treated by the expression:

$$\text{CONSUMPTION} = C_m V_m + C_i V_i - C_f (V_m + V_i) \text{ in mg;}$$

deducing ozone demand of said water to be treated by the expression:

$$\text{ozone demand} = \text{CONSUMPTION}/V_i \text{ in mg/l;}$$

choosing a level of treatment T greater than the value of the ozone demand.

3. The method according to claim 2, further comprising choosing said level of treatment T greater than the value of the ozone demand by:

i) selecting a known value of the residual oxidants and/or dissolved ozone residue desired by an application under consideration for said water to be treated in its final use;

ii) evaluating a minimum journey time $\Delta T_{min}$ between a treatment point and a final user point for the application under consideration of said water to be treated;

iii) evaluating presence of the ozone in the water to be treated by measuring, in accordance with step d), at time intervals after the addition, the content $C_f$ of residual oxidants and/or dissolved ozone in the samples after the addition of $V_m$; and iv) choosing a level of treatment T as a function of said residual oxidants and/or dissolved ozone residue desired by the application under consideration and of the content $C_f$ measured during the preceding stage iii) after an interval $\Delta T_{min}$ after the addition of $V_m$.

4. The method according to claim 1, wherein said liquid to be treated is a seawater, the method comprising carrying out successive iterations in order to determine a maximum volume $V_m^{max}$ of said withdrawn portion which makes it possible to obtain, immediately after addition, a value of the content $C_f$ substantially identical to that of the content $C_i$, as follows:

if $C_f$ is greater than $C_i$, repeating steps c) and d) with a withdrawn portion with a volume of $V_n$, $V_n$ being less than $V_m$, until a value of the content $C_f$ is obtained which is substantially identical to that of the content $C_i$;

if $C_f$ is substantially identical to $C_i$, repeating the steps c) and d) with a withdrawn portion with a volume of $V_n$, $V_n$ being greater than $V_m$, as long as the value of the content $C_f$ is substantially identical to the content $C_i$;

choosing a level of treatment T equal to $C_m V_m^{max}/V_i$.

5. The method according to claim 1, wherein said liquid to be treated is a seawater, the method comprising:

carrying out successive iterations in order to determine a maximum withdrawal volume $V_m^{max}$ which makes it possible to obtain, after a predetermined time $\Delta T$ after said addition, a value of the content $C_f$ substantially identical to that of the content $C_i$, as follows:

if $C_f$ is greater than $C_i$, repeating steps c) and d) with a withdrawn portion with a volume of $V_n$, $V_n$ being less than $V_m$, until, after said predetermined time $\Delta T$, a value of the content $C_f$ is obtained which is substantially identical to that of the content $C_i$;

if $C_f$ is substantially identical to $C_i$, repeating the steps c) and d) with a withdrawn portion with a volume of $V_n$, $V_n$ being greater than $V_m$, as long as the value of the content $C_f$ is, after the said predetermined time $\Delta T$, substantially identical to the content $C_i$;

choosing a level of treatment T equal to $C_m V_m^{max}/V_i$, and holding the water thus treated in a reactor using said level of treatment T, capable of holding the water thus treated for a time of at least $\Delta T$, before any subsequent use of the water thus treated.

* * * * *